United States Patent
Huang (10) Patent No.: US 6,594,512 B2
(45) Date of Patent: Jul. 15, 2003

(54) METHOD AND APPARATUS FOR ESTIMATING A PHYSIOLOGICAL PARAMETER FROM A PHYSIOLOGICAL SIGNAL

(75) Inventor: John W. Huang, Peabody, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/915,610

(22) Filed: Jul. 26, 2001

(65) Prior Publication Data

US 2002/0099280 A1 Jul. 25, 2002

Related U.S. Application Data

(60) Provisional application No. 60/252,229, filed on Nov. 21, 2000.

(51) Int. Cl.[7] ............................................. A61B 5/00
(52) U.S. Cl. ....................... 600/324; 600/323; 600/336
(58) Field of Search ................................ 600/309–310, 600/322–326, 330, 336

(56) References Cited

U.S. PATENT DOCUMENTS 5,632,272 A    5/1997  Diab et al.
6,002,952 A   12/1999  Diab et al. .................. 600/310
6,022,321 A  *  2/2000  Amano et al. ............... 600/500
6,094,592 A    7/2000  Yorkey et al.
6,122,535 A  *  9/2000  Kaestle et al. .............. 600/322
6,393,311 B1 *  5/2002  Edgar, Jr. et al. ........... 600/323

FOREIGN PATENT DOCUMENTS

EP    1 038 497 A1    9/2000

* cited by examiner

Primary Examiner—Eric F. Winakur
Assistant Examiner—Matthew Kremer
(74) Attorney, Agent, or Firm—Alexander Burke (57) ABSTRACT

A system is disclosed which first identifies a plurality of characteristics of a physiological signal any one of which may represent a physiological parameter. A plurality of different techniques are used to provide respective likelihood factors for each such identified characteristic. The resulting likelihood factors are then analyzed to select the one characteristic of the physiological signal which most likely represents the desired physiological parameter. The physiological parameter is then calculated from the selected characteristic of the physiological signal.

24 Claims, 8 Drawing Sheets

METHOD AND APPARATUS FOR ESTIMATING A PHYSIOLOGICAL PARAMETER FROM A PHYSIOLOGICAL SIGNAL

This is a non-provisional application of provisional application Ser. No. 60/252,229 by J. Huang filed Nov. 21, 2000.

FIELD OF THE INVENTION

The present invention relates to techniques for estimating a physiological parameter from a physiological signal. More specifically, the invention relates to detecting and estimating oximetry signals from physiological signals which include noise, and even more specifically to techniques for accurately determining the pulse rate from noisy physiological signals.

BACKGROUND OF THE INVENTION

It is well known that physiological parameters (e.g. blood oxygen saturation and pulse rate) are represented by physiological signals, and that such signals often contain substantial noise components, often much larger than the physiological signal component. For example, the blood oxygen saturation ($SpO_2$) level in the blood stream may be determined by shining red and infrared (IR) light on a blood perfused part of a patient's body (e.g. finger or earlobe). The light passing through, or reflected off, the patient is detected and signals representing the received light are generated. These signals are then processed to generate both an indication of the pulse rate and the blood oxygen level of the patient.

One problem with such systems is a noise component in the light representative signals. This noise component is substantially caused by movement by the patient, however electromagnetic interference from surrounding equipment, and reception of ambient light by the light sensors also contribute to the noise component. In some cases, this noise component can be substantially large, compared to the signal component. Systems were designed to detect the signal components in the light representative signals in the presence of a relatively large noise component.

Recently, techniques using fast Fourier transforms (FFT) of the light representative signals have been developed. In U.S. Pat. No. 5,632,272, issued May 27, 1997 to Diab et al., data from an FFT of the light representative signals is analyzed to determine the arterial blood saturation. In this patent information from all the FFT frequencies above a threshold level is analyzed with equal weight.

In U.S. Pat. No. 6,094,592, issued Jul. 25, 2000 to Yorkey et al., generates a ratio signal having a value corresponding to each frequency location in the FFT spectrum, then generates a histogram of the values of the ratio signal weighted by the magnitude of the IR FFT at the frequency associated with the ratio value.

In all of these systems, the FFT signal was processed according to an algorithm and a pulse rate signal and $SPO_2$ signal generated. However, there are always clinical situations in which a particular algorithm will perform poorly, and conversely other clinical situations in which that algorithm will perform well. A system which can operate optimally over a range of different clinical situations is desirable.

BRIEF SUMMARY OF THE INVENTION

In accordance with principles of the present invention, a system first identifies a plurality of characteristics of a physiological signal any one of which may represent a physiological parameter. A plurality of different techniques are used to provide respective likelihood factors for each such identified characteristic. The resulting likelihood factors are then analyzed to select the one characteristic of the physiological signal which most likely represents the desired physiological parameter. The physiological parameter is then calculated based on the selected characteristic of the physiological signal.

More specifically, a system according to principles of the present invention determines the parameter of pulse rate from $SpO_2$ physiological signals, which include red and IR light representative signals. The frequency locations of peaks in the spectrum of the IR light representative signal are detected as the characteristics. A plurality of different techniques each generate a likelihood factor for each identified peak, respectively. All of the likelihood factors are then analyzed to select one of the identified peaks as the characteristic most likely representing the actual pulse rate. The pulse rate parameter is calculated from the red and IR light representative signals at the frequency location of the selected peak. The red and IR signals at the frequency location of the selected peak may be further processed to generate a second parameter of the $SpO_2$ value.

BRIEF DESCRIPTION OF THE DRAWING

In the drawing:

FIG. 4a is a functional block diagram illustrating processing for updating the PDFs as illustrated in FIG. 3, and FIG. 4b and FIG. 4c are PDFs useful in understanding the operation of the block diagram illustrated in FIG. 4a;

FIG. 6a is a more detailed block diagram of an IR half period shift circuit, and FIGS. 6b and c are waveform diagrams useful in understanding the operation of the IR half period shift circuit illustrated in FIG. 6a;

FIG. 7a is a more detailed block diagram of an IR full period shift circuit, and FIGS. 7b and c are waveform diagrams useful in understanding the operation of the IR full period shift circuit illustrated in FIG. 7a; and FIG. 8a is a more detailed block diagram of an IR/Red difference circuit, and FIGS. 8b and C is a waveform diagram useful in understanding the operation of the IR/Red difference circuit illustrated in FIG. 8a.

DETAILED DESCRIPTION OF THE INVENTION

Figure 1:
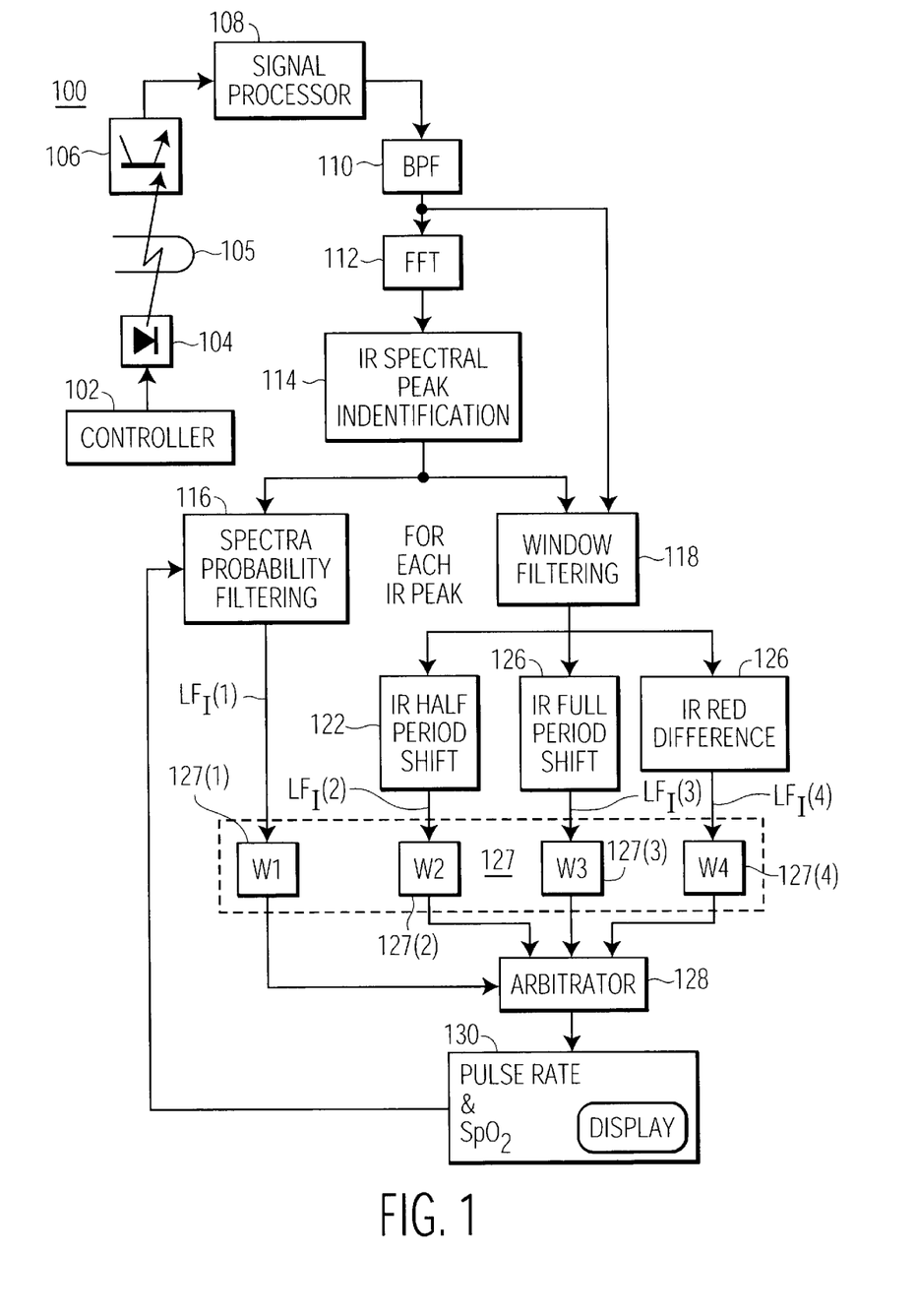
FIG. 1 is a functional block diagram illustrating processing in accordance with principles of the present invention.

FIG. 1 is a functional block diagram illustrating processing for determining the pulse rate and $SPO_2$ values from physiological signals according to principles of the present invention. One skilled in the art will understand that this processing may be performed by dedicated hardware circuitry, or may be performed within a processor operating under control of a control program, or a combination of these techniques. The particular implementation technique is not germane to the present invention.

In FIG. 1, an output terminal of a controller 102 is coupled to a light emitting device 104. In a preferred embodiment, the light emitting device 104 is a set of light emitting diodes (LEDs), as indicated by the schematic symbol in block 104. The light emitting device 104 includes at least one LED for emitting red light, and one LED for emitting infrared (IR) light. Other LEDs, emitting other color light, may also be included. Some portion of the light emitted by the light emitting device 104 is received by a light sensor device 106, as illustrated by the light indicative line between the light emitting device 104 and the light sensor 106. In a preferred embodiment, the light sensor is a phototransistor, as indicated by the schematic symbol in block 106. The light sensor 106 receives the portion of the light from the light emitting device 104 and generates an electrical signal at an output terminal representing the intensity of the received light. The combination of the light emitting device 104 and the light sensor 106 form a blood oxygen concentration sensor 100 of known design.

The output terminal of the light sensor 106 is coupled to an input terminal of a signal processor 108. An output terminal of the signal processor 108 is coupled to a signal input terminal of a bandpass filter BPF 110. An output terminal of the BPF 110 is coupled to an input terminal of a fast Fourier transform (FFT) circuit 112 and a first input terminal of a window filtering circuit 118. An output terminal of the FFT circuit 112 is coupled to an input terminal of an IR spectral peak identification circuit 114. An output terminal of the IR spectral peak identification circuit 114 is coupled to an input terminal of a spectra probability filtering circuit 116 and a second input terminal of the window filtering circuit 118.

An output terminal of the window filtering circuit 118 is coupled to respective input terminals of an IR half period shift circuit 122, an IR full period shift circuit 124, and an IR/red difference circuit 126. An output terminal of the spectra probability filtering circuit 116 is coupled to an input terminal of a first weighting circuit 127 (1). An output terminal of the IR half period shift circuit 122 is coupled to an input terminal of a second weighting circuit 127 (2). An output terminal of the IR full period shift circuit 124 is coupled to an input terminal of a third weighting circuit 127 (3). An output terminal of the IR/red difference circuit 126 is coupled to an input terminal of a fourth weighting circuit 127 (4). The first, second, third and fourth weighting circuits (127 (1), 127 (2), 127 (3), 127 (4)) form a weighting subsystem 127.

Respective output terminals of the first, second, third and fourth weighting circuits (127 (1), 127 (2), 127 (3), 127 (4) are coupled to corresponding input terminals of an arbitrator 128. An output terminal of the arbitrator 128 is coupled to an input terminal of a pulse rate and $SpO_2$ calculating and display circuit 130. An output terminal of the pulse rate and $SpO_2$ calculating and display circuit 130 is coupled to a second input terminal of the spectra probability filtering circuit 116.

In operation, the $SpO_2$ sensor 100, including the light emitting device 104 and light sensor 106, is placed adjacent a blood perfused portion of a patient's body, illustrated in FIG. 1 as 105, such as a finger or ear lobe, in a known manner. The light representative signal produced by the light sensor 106 is relatively low power. The signal processor 108 receives the low power signal and generates a higher power signal in a known manner. In FIG. 1, the signal processor 108 generates two signals, one representing the intensity of red light received by the light sensor 106, and one representing the intensity of IR light received by the light sensor 106. These signals are sampled and converted to digital form by respective digital-to-analog converters (not shown) to generate respective digital signals, all in a known manner. These digital signals are processed in parallel by the remainder of the processing blocks illustrated in FIG. 1, unless explicitly described otherwise below.

The light representative digital signals are first bandpass filtered by the BPF 110 to remove signal components which are not in the range of frequencies within which it is reasonable to expect a pulse frequency. This reduces out-of-band noise, and improves the signal-to-noise ratio of the filtered signal. One skilled in the art will understand how to adjust the passband of the BPF 110 in an appropriate manner.

Figure 2:
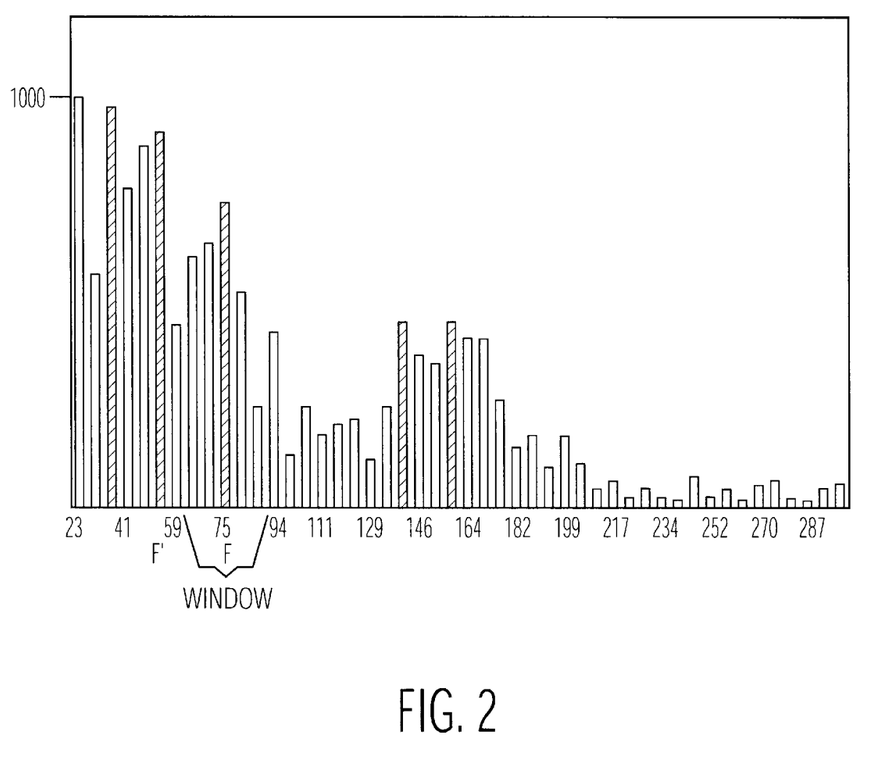
FIG. 2 is a spectrum diagram illustrating an exemplary FFT derived from an IR signal.

The filtered signals (red and IR) are then transformed to the frequency domain by the FFT circuit 112. The FFT circuit 112 produces, in a known manner, successive FFT spectra. Each FFT spectrum consists of a set of 1024 complex values each having a magnitude representing the energy at a respective frequency location. FIG. 2 is a spectrum diagram illustrating an exemplary FFT derived from an IR signal including a relatively limited number of frequency locations. The horizontal direction in FIG. 2 represents frequency and the vertical direction represents magnitude. Each frequency location in the FFT is represented by a vertical rectangle having a horizontal location representing the frequency, and a height representing the magnitude of the FFT at that frequency. The numbers along the horizontal axis represent the pulse rate expressed in beats per minute (BPM). In the illustrated embodiment, a 1024 point FFT is calculated every 10 seconds for each of the red and IR digital signals from the signal processor 108. Consequently, the sampling rate is around 100 samples per second. In the illustrated embodiment, therefore, each FFT consists of a set of 1024 complex values at frequency locations spaced every 0.01 Hz starting from DC to around 100 Hz. However, for the application of determining the pulse rate, only those frequencies from DC to around 5 Hz (300 BPM) are of interest.

In function block 114, magnitudes and frequency locations of peaks in the IR spectrum from the FFT circuit 112 are identified, in a known manner. First, the magnitudes in the FFT are normalized to a predetermined value. That is, the maximum magnitude in the FFT spectrum is set to the predetermined value, and the remainder scaled appropriately in a known manner. In FIG. 2, the maximum magnitude (illustrated at the lowest frequency location) is set to 1000, and the rest are scaled appropriately.

Second, peaks are identified. In the illustrated embodiment, to be identified as a peak, the magnitude of an IR spectral location must (1) be higher than a predetermined threshold magnitude, and (2) be represented by a rise and fall of greater than some predetermined magnitude value on either side of the location. Each FFT spectral location satisfying these criteria is identified as a peak in a known manner. A list of magnitudes and spectral locations of the identified IR peaks is generated. In FIG. 2, peaks are identified at around 35 BPM, 46 BPM, 76 BPM, 140 BPM, and 160 BPM. It is further possible to limit the number of identified peaks for further processing. For example, in the illustrated embodiment only the 20 peaks with the largest magnitudes will be processed. In FIG. 2, identified peaks are illustrated by filled rectangles, while non-peak frequency locations are illustrated by empty rectangles.

In general, the FFT information at each spectral location identified as an IR peak, and possibly other information, as described below, is processed to determine a set of four likelihood factors LFs: one from each of the spectra probability filtering circuit 116 (LF(1)), the IR half period shift circuit 122 (LF(2)), the IR full period shift circuit 124 (LF(3)), and the IR/red difference circuit 126 (LF(4)). That is, a first set of four LFs ($LF_1(1)$, $LF_1(2)$, $LF_1(3)$, $LF_1(4)$) is generated for IR FFT peak 1, a second set of four LFs ($LF_2(1)$, $LF_2(2)$, $LF_2(3)$, $LF_2(4)$) is generated for IR FFT peak 2 and so forth. In the remainder of this application, the notation $LF_i(j)$ will refer to the likelihood factor LF for the $i^{th}$ IR FFT peak from the $j^{th}$ processing function.

More specifically, referring again to FIG. 2, a first set of four LFs ($LF_1$) is produced by the spectra probability filtering circuit 116, the IR half period shift circuit 122, the IR full period shift circuit 124, and the IR/red difference circuit 126, for the 35 BPM spectral location, identified as a peak in the IR FFT, as described above. A second set of four LFs ($LF_2$) is produced for the 46 BPM spectral location; a third set ($LF_3$) for the 76 BPM spectral location, and so on for the 140 BPM ($LF_4$), and 160 BPM ($LF_5$) spectral locations.

Each set of four $LF_i$s ($LF_i(1)$, $LF_i(2)$, $LF_i(3)$, and $LF_i(4)$) is then weighted by the corresponding weighting circuit in the weighting subsystem 127. That is, each $LF_i(1)$ is weighted by the weight W1 in weighting circuit 127(1) to generate a corresponding weighted likelihood factor $WLF_i(1)$, each $LF_i(2)$ is weighted by the weight W2 in the weighting circuit 127(2) to generate a corresponding weighted likelihood factor $WLF_i(2)$ and so forth. The result is a set of four $WLF_i$s associated with each of the identified IR spectral peak locations (35 BPM, 46 BPM, 76 BPM, 140 BPM and 160 BPM).

The arbitrator 128 processes all of the sets of $WLF_i$s associated with all of the IR spectral peak locations, and selects one of the IR spectral peak locations as the frequency most likely to represent the pulse rate. One skilled in the art will understand that there are many different ways in which the WLFs may be processed to select the pulse rate representative frequency. For example, the arbitrator 128 may normalize the WLFs, identify the WLF having the highest value, and select the IR FFT peak associated with the identified WLF as representing the pulse rate. Alternatively, in a preferred embodiment, the arbitrator 128 forms a combination of the four WLFs associated with a respective IR FFT peak, then selects the IR FFT peak associated with the combination having the highest value as representing the pulse rate. However, the particular selection process used in the arbitrator 128 is not germane to the present invention.

The pulse rate and $SpO_2$ calculating and display circuit 130 processes the FFT information at the frequency selected by the arbitrator 128 in a known manner to calculate the pulse rate, and the $SPO_2$ value corresponding to the selected pulse rate.

In block 116 determination of likelihood factors $LF_i(1)$ is based on probabilistic filtering. A probability density function (PDF) of pulse rate frequencies is maintained based on previously identified pulse rates and $SPO_2$ values, as received from the $SpO_2$ calculating and display circuit 130. The respective probabilities, running from zero to one, in this PDF at each of the frequency locations of the IR peaks identified in block 114 are the LFs for that IR peak. The PDF is then updated, all in a manner to be described in more detail below.

Figure 3A:
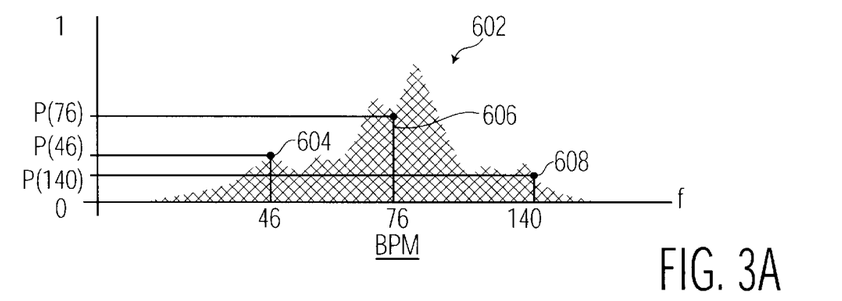
FIGS. 3a through d are diagrams of probability distribution functions (PDFs) useful in understanding the operation of the spectra probability filtering circuit illustrated in FIG. 1.

FIG. 3a is a diagram of a PDF useful in understanding the operation of the spectra probability filtering circuit 116 illustrated in FIG. 1. In FIG. 3a, a PDF 602 is illustrated by cross hatching. The horizontal axis represents pulse rate in beats per minute, and the vertical axis represents the probability from zero to one. The PDF 602 in FIG. 3a is illustrated in continuous form. However, one skilled in the art will understand that in the illustrated embodiment the PDF 602 is discrete, containing a set of N probability representative entries, each having a value ranging from zero to one, corresponding to the set of frequency locations in each of the FFTs from the FFT circuit 112. As described above, in the illustrated embodiment, there are N=1024 frequency locations in the FFTs from the FFT circuit 112, and consequently 1024 corresponding frequency locations in the PDF 602 illustrated in FIG. 3a.

In FIG. 3a, three peaks from the IR FFT are illustrated: one 604 at 46 BPM, one 606 at 76 BPM and one 608 at 140 BPM. Each of these peaks is represented by a vertical line. The horizontal location of the line represents the frequency of the peak, and the height of the line is the probability of the PDF 602 at that frequency location. The line 604, representing the peak at 46 BPM, has the probability P(46); the line 606, representing the peak at 76 BPM, has the probability P(76); and the line 608, representing the peak at 140 BPM, has the probability P(140). In FIG. 3, a first likelihood factor, $LF_1(1)$, associated with the 46 BPM frequency has a value of P(46), a second $LF_2(1)$, associated with the 76 BPM frequency, has a value of P(76), and a third $LF_3(1)$, associated with the 140 BPM frequency, has a value of P(140). As described above, after the LFs have been determined, the PDF 602 is updated.

Figure 4A:
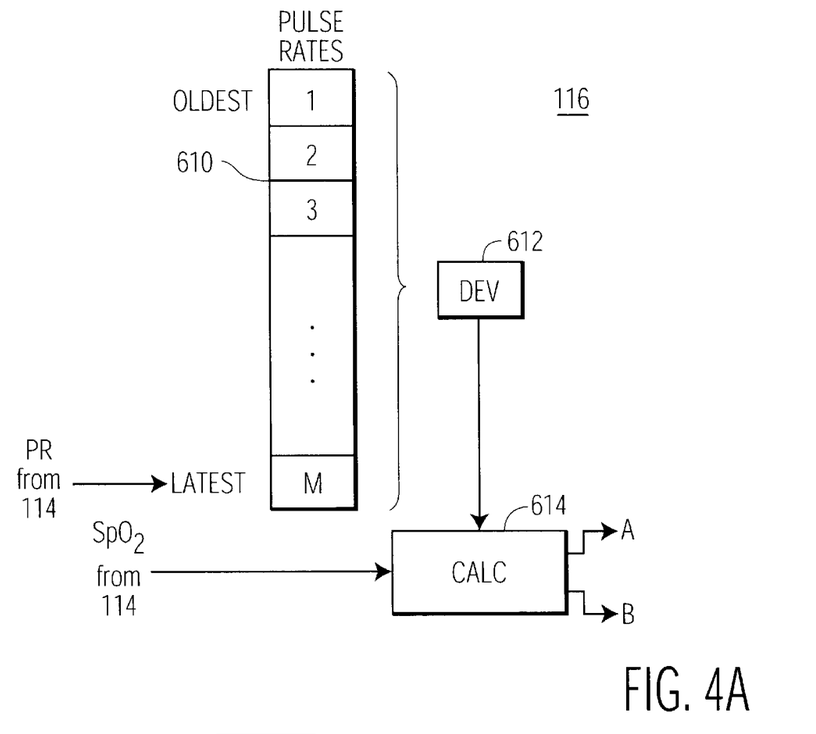
Figure 4B:
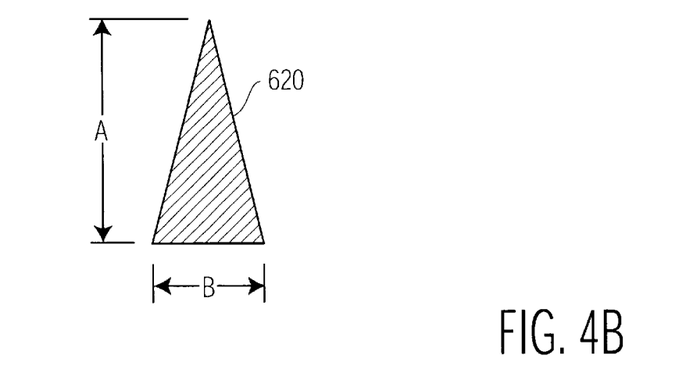

FIG. 4a is a functional block diagram illustrating how the PDF 602 of FIG. 3a is updated, and FIG. 4b and c are illustrations of PDFs useful in understanding the operation of FIG. 4a. In FIG. 4a, pulse rate values from the pulse rate and $SpO_2$ calculation and display circuit 130 (of FIG. 1) are entered into a list 610 of such values. The list is processed by a deviation measure calculating block 612. An output from the deviation measure calculating block 612 is coupled to an input of a PDF parameter calculating circuit 614. $SpO_2$ values from the pulse rate and $SpO_2$ calculation and display circuit 130 are supplied to another input of the parameter calculating circuit 614. The parameter calculating circuit 614 calculates two parameters, A and B in a manner described in detail below. The parameters A and B are used to produce a new PDF 620.

In FIG. 4a, the list 610 of pulse rate values, containing M entries, is maintained. These pulse rate values are the final pulse rate values reported to the user and displayed on the display device by the pulse rate and $SPO_2$ calculation and display circuit 130. As each new pulse rate value is received from the pulse rate and $SpO_2$ calculation and display circuit 130, the oldest value is discarded from the list 610 and replaced with the new value.

A measure of the deviation Dev, or spread, of these M pulse rate values is calculated in block 612. To maintain statistical accuracy there is a minimum value for M, which in the illustrated embodiment is around 10. To minimize computation time, there is also a maximum value for M, which in the illustrated embodiment is around 30. The deviation Dev may be represented by the standard deviation in a normal manner. That is, a mean $\bar{p}$ is first calculated from the list 610 of pulse rate values, then the standard deviation from that mean value $\bar{p}$ is calculated, both in the known manner. Alternatively, the deviation of the pulse rate values in the list 610 from the latest pulse rate value $\hat{p}$ from the pulse rate and $SpO_2$ calculation and display circuit 130 may be calculated as $$Dev = \frac{1}{M-1} \sum_{i=1}^{M} (p_i - \hat{p}),$$

where $p_i$ represents the $i^{th}$ entry in the list 610. For example, if the IR peak 606 at 76 BPM was selected by the pulse rate and $SPO_2$ calculation and display circuit 130 in the previous iteration as representing the pulse rate $\hat{p}$, then the deviation of the pulse rate values in the list 610 around the frequency location $\hat{p}$ representing 76 BPM is calculated in block 612.

A low Dev value represents a situation in which the $SpO_2$ signals are clean and relatively noise free, and in which no external factors, such as patient movement, are degrading pulse rate and $SPO_2$ readings. The readings in this case are relatively stable, and have a relatively small spread in frequency. A high Dev value represents a situation in which the $SPO_2$ signals are noisy, or in which patient movement is degrading the pulse rate and $SpO_2$ readings. The readings in this situation can change rapidly and erratically. This situation can also indicate that the pulse rate is changing relatively rapidly.

Figure 4C:
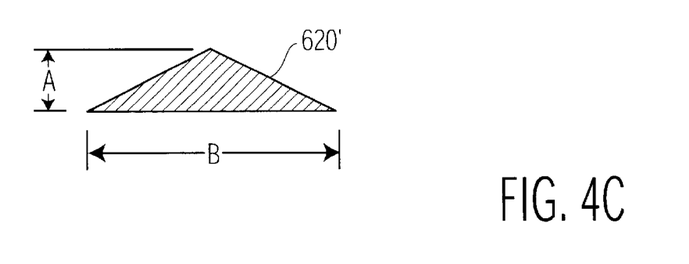

The deviation measure Dev, and the $SpO_2$ value are then used to produce values A and B necessary to generate a new PDF 620, as illustrated in FIGS. 4b and c. The new PDF 620 has a height, represented by the parameter A, and a width, represented by the parameter B. To simplify calculations, in the illustrated embodiment the new PDF is triangular in shape, though one skilled in the art will understand that other PDF shapes may be used as well, such as the known Gaussian shape. The parameter A is calculated as $$A \propto \frac{SpO_2}{Dev}.$$

The parameter B is calculated as B Dev. Thus, the more stable the pulse rate signals, indicated by a relatively low Dev value, the higher and narrower the new PDF, as illustrated in PDF 620. This represents the higher probability that the pulse rate is within a relatively narrow frequency range. This is illustrated in FIG. 4b in which the new PDF 620 is relatively tall and narrow. Conversely, the more erratic and unstable the pulse rate signals, indicated by a relatively high Dev value, the lower and wider the new PDF, as illustrated in PDF 620'. This represents the lower probability of the pulse rate being at any particular frequency, but instead that the pulse rate is somewhere within a relatively wide range of frequencies. This is illustrated in FIG. 4c in which the new PDF 620' is relatively short and wide.

Figure 3B:
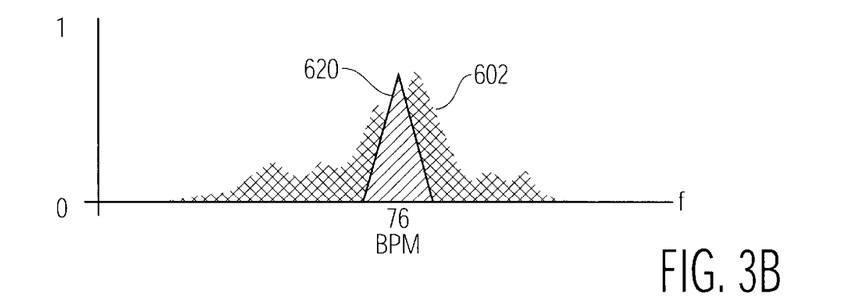

The PDF 602 is then updated using this new PDF 620. In the illustrated embodiment the relatively tall and narrow PDF 620, as illustrated in FIG. 4b, is used. Referring back to FIG. 3b, the new PDF 620 is inserted into the preexisting PDF 602 of FIG. 3a. The new PDF 620 is centered at the frequency selected by the pulse rate and $SpO_2$ calculation and display circuit 130. In the illustrated embodiment this is the frequency location corresponding to a pulse rate of 76 BPM. The resulting PDF 602' is illustrated in FIG. 3c.

Figure 3C:
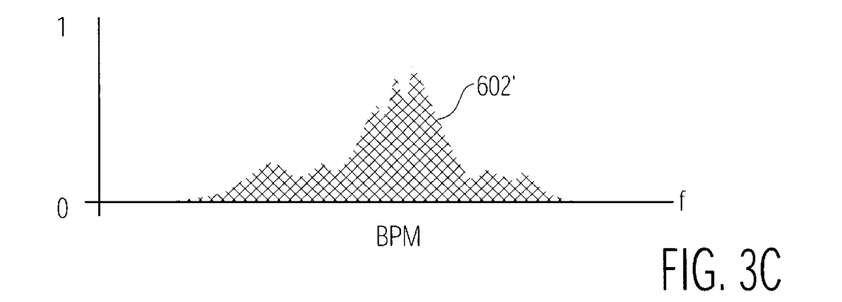

The magnitude of the PDF 602' of FIG. 3c is then reduced by a factor $$f \propto \frac{1}{Dev}.$$

Figure 3D:
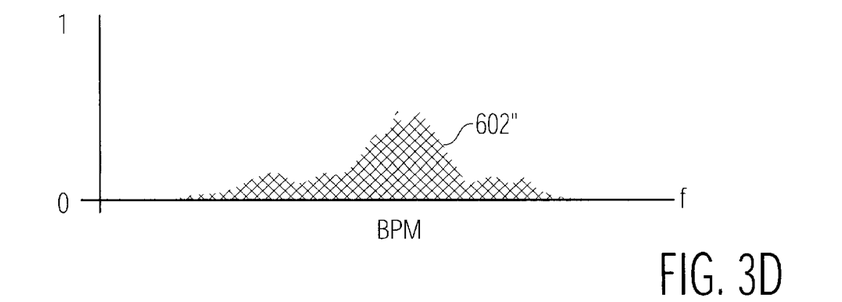

As described above, a low Dev value indicates relatively clean signals and stable pulse rate, while a high Dev value indicates relatively noisy signals, or erratic and/or rapidly changing pulse rate. The lower the Dev value, indicating clean signals and stable pulse rate, the higher the factor f and the more the PDF is reduced. This results in a narrow PDF which loses much of its information with each iteration, enabling the spectra probability filter 116 to follow changes in the pulse rate more easily. The higher the Dev value, indicating noisy signals or erratic pulse rate, the lower the factor f, and the less the PDF is reduced. This results in a wider PDF which retains most of its information from iteration to iteration. FIG. 3d illustrates the resulting PDF 602", which is then used to determine LFs for the next set of IR peak values from the IR peak identification circuit 114, as illustrated in FIG. 3a.

In function block 118, for each IR peak identified, the red and IR signals are filtered by a window filter having a relatively narrow passband surrounding the frequency location F of that peak. Any of the number of known implementations of window filters may be used. For example, referring to FIG. 2, the FFT value at the frequency location F, and FFT values for a predetermined number of surrounding frequency locations are selected, while the FFT values for all the other frequency locations are ignored. An inverse Fourier transform of the selected FFT frequency values is then performed to generate respective ten second, window filtered, time domain signals representing the red and IR signals in the frequency neighborhood of the selected peak.

Figure 5:
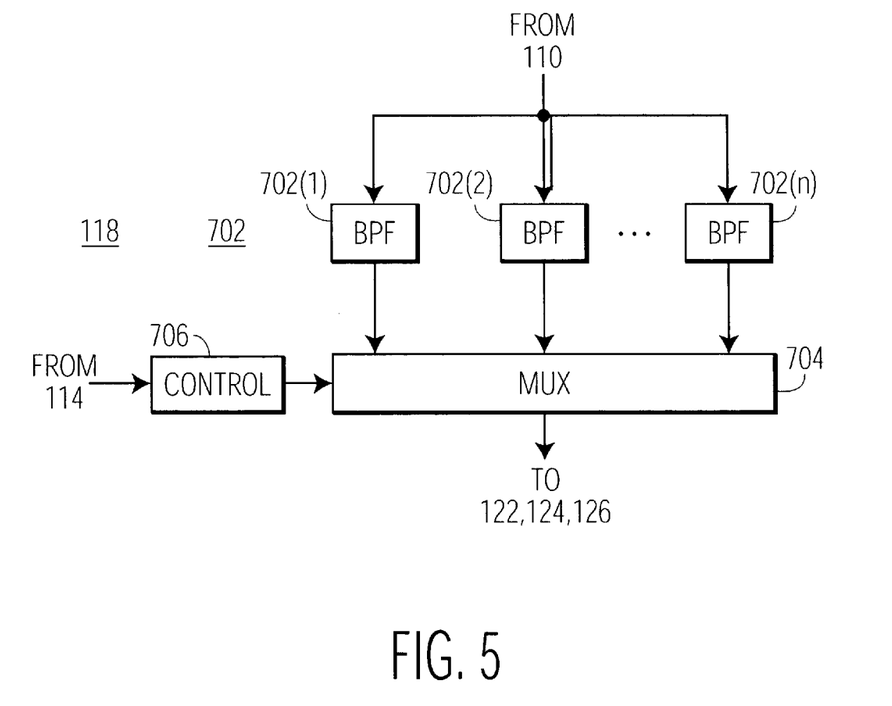
FIG. 5 is a block diagram of a window filter which may be used in the embodiment of the present invention illustrated in FIG. 1

FIG. 5 illustrates an alternative, preferred implementation of a window filter 118. The illustrated window filter 118 may be used to filter both the red and IR light representative signals. In FIG. 5, the bandpass filtered light representative signal from the bandpass filter 110 is coupled to respective input terminals of a plurality 702 of n bandpass filters. Respective output terminals of the plurality 702 of bandpass filters are coupled to corresponding input terminals of a multiplexer 704. An output terminal of the multiplexer 704 is coupled to the processing circuitry: IR half period shift circuit 122, the IR full period shift circuit 124 and the IR/red difference circuit 126. A signal representing the frequency of the IR peak currently being processed from the IR spectral peak identification circuit 114 is coupled to an input terminal of a control circuit 706. An output terminal of the control circuit 706 is coupled to a control input terminal of the multiplexer 704.

In operation, each one of the plurality 702 of bandpass filters has a relatively narrow passband, and the plurality 702 have respective center frequencies selected so that the entire frequency range of interest (i.e. DC to around 5 Hz) is covered. In the illustrated embodiment, there are nine bandpass filters 702(1) to 702(9). All of the bandpass filters 702 have a passband of around 1 Hz. The first bandpass filter 702(1) has a center frequency of around 0.5 Hz and a passband of DC to around 1 Hz. The second bandpass filter 702(2) has a center frequency of around 1 Hz and a passband of from around 0.5 Hz to around 1.5 Hz, and so forth. The ninth bandpass filter 702(9) has a center frequency of around 4.5 Hz and a passband of from around 4 Hz to around 5 Hz. The respective passbands of the plurality 702 of bandpass filters, therefore, overlap.

The control circuit 706 receives a signal representing the frequency of the IR peak currently being processed. The control circuit 706 then selects the bandpass filter 702 having a center frequency which is closest to the IR peak frequency, and conditions the multiplexer 704 to couple the selected bandpass filter 702 to its output terminal, and, thus, to the processing circuitry IR half period shift circuit 122, the IR full period shift circuit 124 and the IR/red difference circuit 126.

Figure 6A:
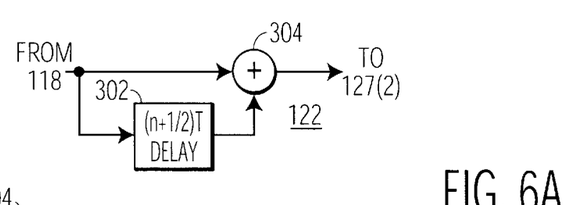
Figure 6B:
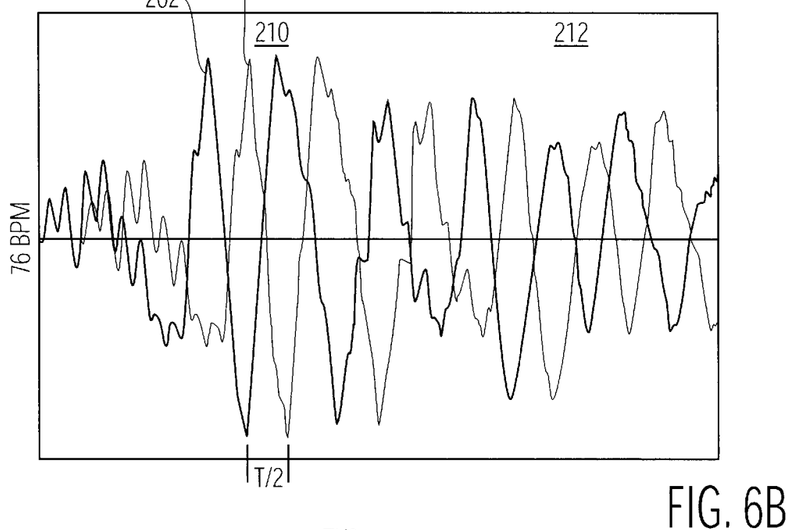

FIG. 6a is a more detailed block diagram of an IR half period shift circuit 122, and FIG. 6b and c are waveform diagrams useful in understanding the operation of the IR half period shift circuit illustrated in FIG. 6a. In FIG. 6a, the window filtered IR signal from the window filtering circuit 118 (of FIG. 1) is coupled to an input terminal of a delay circuit 302 and a first input terminal of an adder 304. An output terminal of the delay circuit 302 is coupled to a second input terminal of the adder 304. An output terminal of the adder 304 is coupled to the second weighting circuit 127(2) (of FIG. 1).

A pulse oxymetry IR signal component (i.e. without a noise component) of the window filtered oximetry signal at or near the actual frequency of the pulse rate is symmetrical in each period. That is, each pulse waveform is similar in form to a sine wave, with equal height peaks and troughs spaced equally in time. Consequently, provided the heart rate remains constant, a pulse oxymetry signal component waveform shifted one half cycle will appear to be an inverted version of the unshifted waveform. Further, this remains true for any shift of n+½ cycles, where n is an integer. The sum of the shifted and unshifted signal, therefore, will be substantially close to zero.

In the presence of noise, the cancellation will be incomplete. However, only the signal represented by the FFT peak at or near the frequency of the actual pulse rate contains a pulse oxymetry signal component in addition to the noise component. For this peak, the pulse rate component will be substantially canceled. For all other peaks, there is no such component to be canceled and the resulting signals from those peaks will tend to remain greater than those from the peak containing the signal component.

In FIG. 6, in function block 122 operates separately on each peak identified in the IR FFT spectrum by the peak identification block 114 (of FIG. 1). For each peak, a cycle period T is calculated as 1/F, where F is the frequency location of the peak in Hertz. A version of the window filtered time domain signal for that peak, delayed by T/2, is then generated by the delay circuit 302. This delayed signal is added to the original window filtered time domain signal by the adder 304, which operates as an accumulator. The result of the accumulation by adder 304 is the $LF_i(2)$ for this frequency, and is supplied to the weighting circuit 127(2). The weight W2 applied by the weighting circuit 127(2) is a negative weight, consequently giving a higher weight (less negative) to the signal with the lowest accumulation, on the assumption that that signal is most likely to have had a signal component canceled, as described above.

FIG. 6b illustrates an IR waveform for the FFT spectral peak at the frequency location corresponding to 76 BPM (F≈1.25 Hz). This waveform has been window filtered with a passband from 1 Hz to 2 Hz. The cycle period for this waveform is T=1/F≈0.8 seconds. The window filtered waveform is illustrated as a darker line 202, and represents the signal from the window filter 118. The delayed signal is illustrated by a lighter line 204 and is the waveform 202 delayed by a time T/2. When the delayed signal 204 is added to the undelayed signal 202, the result will be relatively close to zero, especially in the time areas 210 and 212, where the noise component is low and the delayed signal 204 more closely approximates the inverse of the undelayed signal 202. An accumulated summation of these two signals, representing the LF for this IR peak frequency, will be relatively small.

Figure 6C:
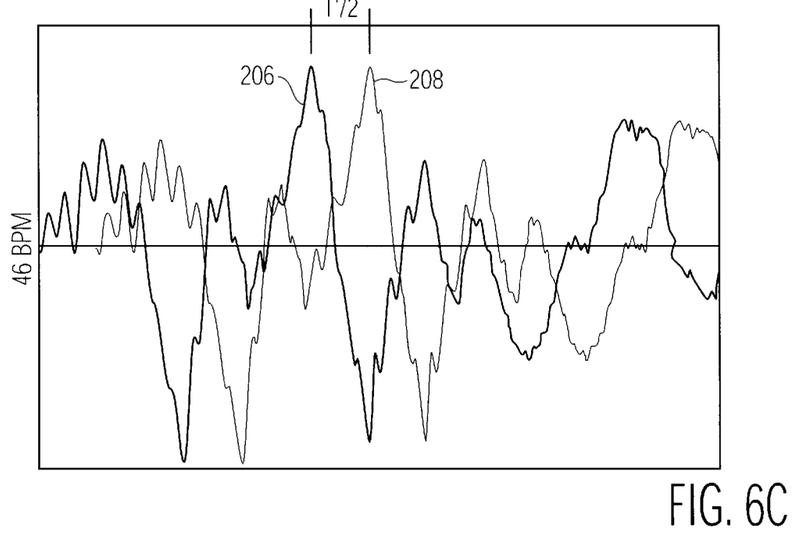

FIG. 6c illustrates an IR waveform for the FFT spectral peak at the frequency location corresponding to 46 BPM (F'≈0.75 Hz). This waveform has been window filtered having a passband from 0.5 Hz to 1.5 Hz. The cycle period for this waveform is T'=1/F'≈1.3 seconds. The window filtered waveform is illustrated as a darker line 206, and the delayed signal is illustrated by a lighter line 208 delayed by a time T'/2. When the delayed signal 208 is added to the undelayed signal 206, the result is not as close to zero because the delayed signal 208 does not approximate the inverse of the undelayed signal 206. The accumulated summation of these two signals will be relatively large, or at least larger than that for the signals illustrated in FIG. 6b.

An accumulation is performed for each IR FFT spectral peak identified by block 114 (of FIG. 1) and the LF(2) for each peak is saved along with the frequency and magnitude of that peak. The LF(2)s for all the identified IR FFT peaks are then supplied to the second weighting circuit 127(2). As described above, the cancellation effect of the pulse oxymetric signal will occur at all half period shift times. That is for (n+½)T, where n is an integer. Thus, it is possible to repeat the accumulation process for more than one half period shift, e.g. for T/2, 3T/2, 5T/2 etc. The total accumulation for all such half period shift times then forms the LF(2) for this frequency peak, and is weighted as described above.

Figure 7A:
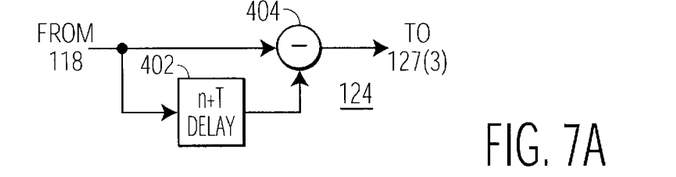
Figure 7B:
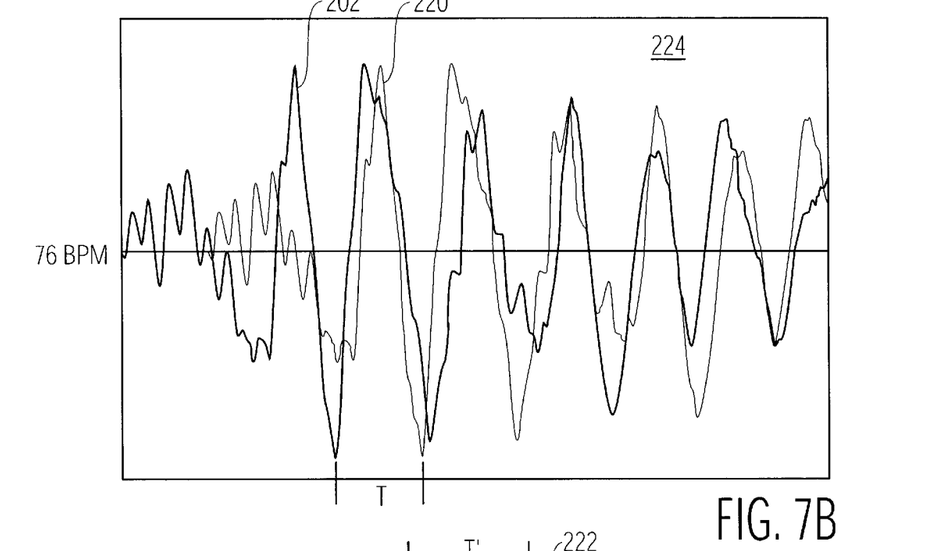

FIG. 7a is a more detailed block diagram of an IR full period shift circuit 124, and FIGS. 7b and c are waveform diagrams useful in understanding the operation of the IR full period shift circuit illustrated in FIG. 7a. In FIG. 7a, the window filtered IR signal from the window filtering circuit 118 (of FIG. 1) is coupled to an input terminal of a delay circuit 402 and a first input terminal of an subtractor 404. An output terminal of the delay circuit 402 is coupled to a second input terminal of the subtractor 404. An output terminal of the subtractor 404 is coupled to the third weighting circuit 127(3) (of FIG. 1).

A pulse oxymetry signal component of the window filtered oximetry IR signal at or near the actual frequency of the pulse rate is cyclical with a periodicity related to the actual pulse rate. As described above, each pulse waveform of the signal component is similar in form to a sine wave, with equal height peaks and troughs spaced equally in time. This signal repeats with every heart beat. Consequently, provided the pulse rate remains constant, a pulse oxymetry signal component waveform shifted one cycle will appear to be the same as the unshifted waveform. Further, this remains true for any shift of n cycles, where n is an integer. The difference between the shifted and unshifted signal, therefore, will be substantially close to zero.

As before, in the presence of noise the cancellation will be incomplete. However, only the signal representing the IR FFT peak at or near the frequency of the actual pulse rate contains a pulse oxymetry signal component in addition to the noise component. For this peak, the pulse rate component will be substantially canceled. For all other peaks, no such component will be canceled and the resulting signals from those peaks will tend to remain greater than those from the peak containing the signal component.

In FIG. 7a, in a similar manner to function block 122 in FIG. 6a, the function block 124 also operates separately on each peak identified in the IR FFT spectrum by the peak identification block 114 (of FIG. 1). A version of the window filtered signal for that peak, delayed by the previously calculated cycle period T, is generated by the delay circuit 402. This delayed signal is subtracted from the original window filtered time domain signal by the subtractor 404, operating as an accumulator. The result of the accumulation by subtractor 404 is the LF(3) associated with that IR FFT peak, and is supplied to the weighting circuit 127(3). The weight W3 applied by the weighting circuit 127(3) is also a negative weight, giving a higher weight (less negative) to the signal with the lowest accumulation, on the assumption that that signal is most likely to have had a signal component canceled, as described above.

FIG. 7b corresponds to FIG. 6b and illustrates the IR waveform for the FFT spectral peak at the frequency location corresponding to 76 BPM (F≈1.25 Hz). As described above, this waveform is illustrated as a darker line 202, has been window filtered having a passband from 1 Hz to 2 Hz, and has a cycle period of T=1/F≈0.8 seconds. The delayed signal, delayed by a time T, is illustrated by a lighter line 220. When the delayed signal 220 is subtracted from the undelayed signal 202, the result will be relatively close to zero, especially in the time area 224, where the noise component is relatively low and the delayed signal 220 more closely approximates the undelayed signal 202. An accumulated difference of these two signals will be relatively small.

Figure 7C:
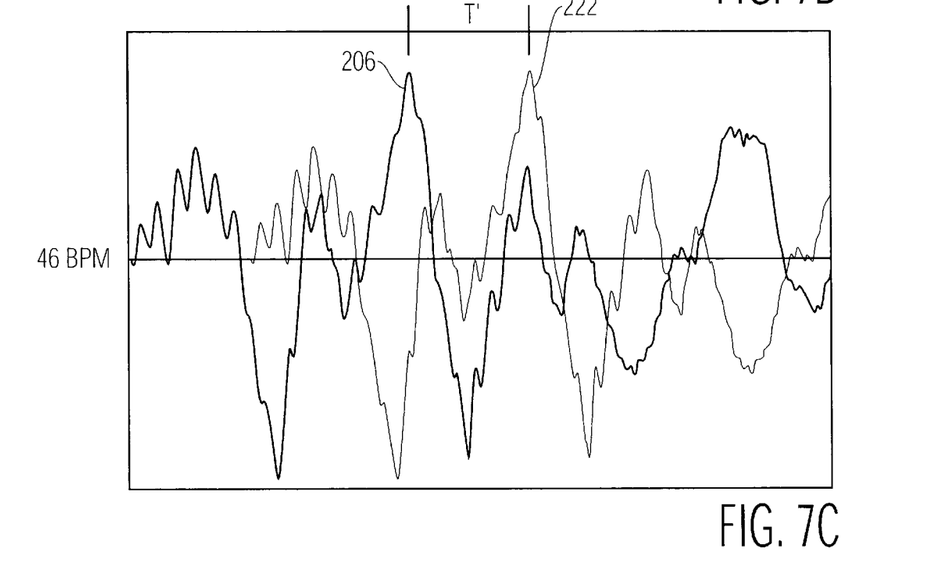

FIG. 7c corresponds to FIG. 6c and illustrates the waveform for the IR FFT spectral peak at the frequency location corresponding to 46 BPM. As described above, this waveform has been window filtered having a passband from 0.5 Hz to 1.5 Hz, has a cycle period of T'=1/F'≈1.3 seconds, and is illustrated as a darker line 206.

The delayed signal, delayed by a time T', is illustrated by a lighter line 222. When the delayed signal 222 is subtracted from the undelayed signal 206, the result is not close to zero because the delayed signal does not approximate the undelayed signal. The accumulated difference of these two signals will be relatively large, or at least larger than that for the signals illustrated in FIG. 7b.

As described above, the cancellation effect of the pulse oxymetric signal will occur at all full period shift times. That is for nT, where n is an integer. Thus, it is possible to repeat the accumulation process for more than one full period shift, e.g. for T, 2T, 3T etc. The total difference accumulation for all such full period shift times is the LF(3) for this frequency, and is weighted as described above.

Figure 8A:
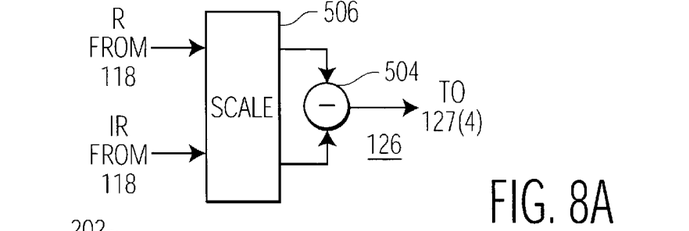
Figure 8B:
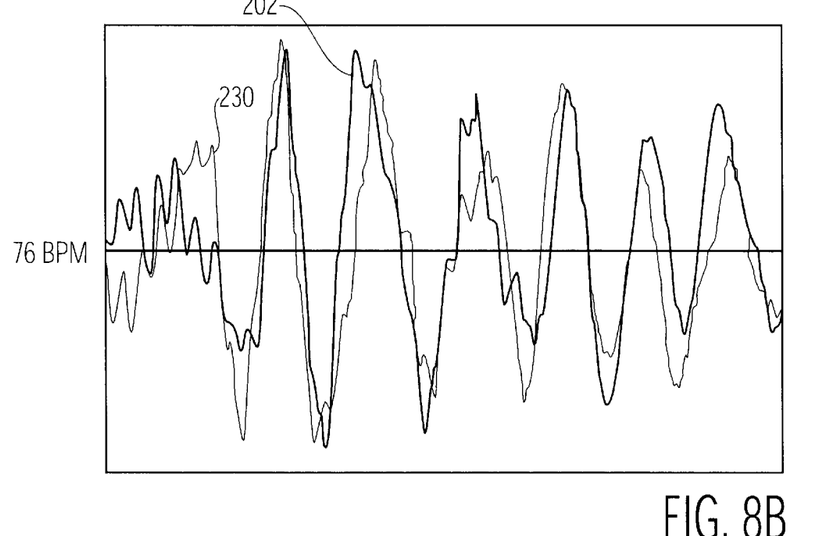
Figure 8C:
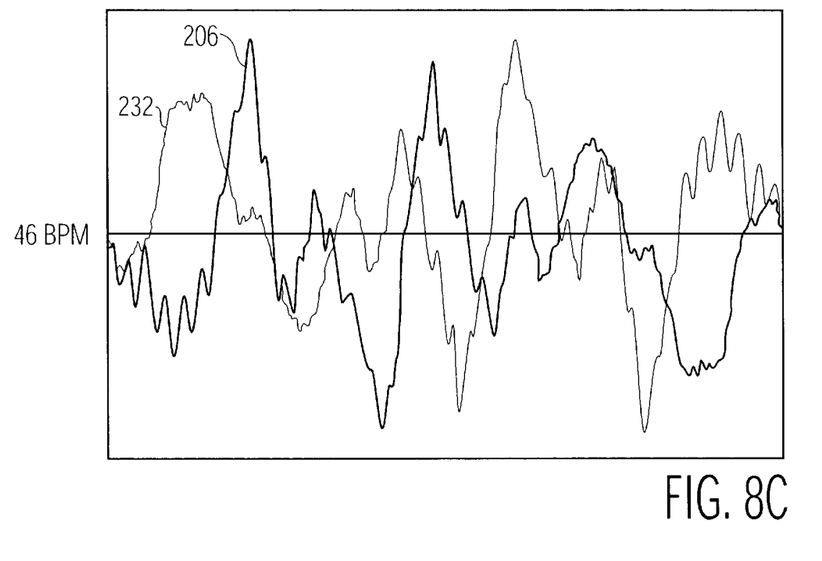

FIG. 8a is a more detailed block diagram of an IR/Red difference circuit 126, and FIG. 8b and FIG. 8c are waveform diagrams useful in understanding the operation of the IR/Red difference circuit illustrated in FIG. 8a. In FIG. 8a, a window filtered red signal (R) and the window filtered IR signal from the window filtering circuit are coupled to respective input terminals of a subtractor 504 via a scaling circuit 506. An output terminal of the subtractor 504 is coupled to the fourth weighting circuit 127(4).

The pulse oxymetry signal component of the window filtered IR oximetry signal at or near the actual frequency of the pulse rate is correlated with the signal component of the window filtered red oximetry signal at the same frequency. That is, the IR and red window filtered pulse oxymetry signal components have substantially congruent waveforms. Thus, the difference between the window filtered red oximetry signal component and the window filtered IR oximetry signal will be relatively close to zero.

As before, in the presence of noise the correlation will be corrupted. However, only the red and IR signals represented by the respective FFT peaks at or near the frequency of the actual pulse rate contain a pulse oxymetry signal component in addition to the noise component. For these peaks, the pulse rate components will be substantially canceled from the difference. For all other peaks, no such component will be canceled and the resulting difference from those peaks will tend to remain greater than that from the peak containing the signal component.

In FIG. 8, in a similar manner to function blocks 122 of FIG. 6 and 124 of FIG. 7, the function block 126 also operates separately on each peak identified in the IR FFT spectrum by the peak identification block 114 (of FIG. 1). The window filtered red signal R is subtracted from the window filtered IR signal by the subtractor 504, operating as an accumulator. One skilled in the art will understand that to minimize skew, and to maximize cancellation, the window filtered red and IR signals must be scaled so that they are approximately of equal magnitudes. The scaling circuit 506 is, thus, conditioned to scale the red and IR signals so that they have equal peak magnitudes. The result of the accumulation by subtractor 504 is the LF(4) for the IR FFT peak, and is supplied to the fourth weighting circuit 127(4). The weight W4 applied by the weighting circuit 127(4) is also a negative weight, giving a higher weight (less negative) to the signal with the lowest accumulation, on the assumption that that signal is most likely to represent the FFT spectral peak having the highest correlation between the red R signal component and the IR signal component.

FIG. 8b corresponds to FIG. 6b and FIG. 7b, and illustrates respective IR and red waveforms for the FFT spectral peak at the frequency location corresponding to 76 BPM. The waveform representing the IR signal is illustrated as a darker line 202, and the waveform representing the red signal is illustrated by a lighter line 230. Because the IR 202 and red 230 signal waveforms are relatively congruent, indicative of a low noise component level and a high level of correlation, when the red signal 230 is subtracted from the IR signal 202, the result will be relatively close to zero. An accumulated difference of these two signals will be relatively small.

FIG. 8c corresponds to FIG. 6c and FIG. 7c and illustrates a respective red and IR waveforms for the IR FFT spectral peak at the frequency location corresponding to 46 BPM. The waveform representing the IR signal is illustrated as a darker line 206, and the waveform representing the red signal is illustrated by a lighter line 232. Because the IR 206 and red 232 signal waveforms are not relatively congruent, indicative of a high noise component level and a low level of correlation, when the red signal 232 is subtracted from the IR signal 206, the result will not be relatively close to zero. The accumulated difference of these two signals will be relatively large, or at least larger than that for the signals illustrated in FIG. 8b.

One skilled in the art will understand that, as described above with reference to the full period shift circuit 124, the red and IR pulse oximetry signal components are repetitive over the full period. The correlation effect of the red and IR pulse oxymetric signal components, thus, will also occur when the red and IR signals are time shifted by full period time intervals relative to each other (not shown to simplify the figure). Thus, it is possible to repeat the accumulation process for one or more such full period shifts, e.g. for T, 2T, 3T etc. The total difference accumulation for all such full period shift times is the LF(4) for that IR FFT peak, and is weighted as described above.

It is known that LFs from some of the processing circuitry, (i.e. some of the spectra probability filtering circuit 116, the IR half period shift circuit 122, the full period shift circuit 124 and the IR/red difference circuit 126) are more accurate than those from others. The weighting subsystem 127 gives more weight to that processing which is more accurate and less to that processing which is less accurate. This weighting may be different for different clinical situations.

TABLE 1

| Weight | W1 | W2 | W3 | W4 |
|---|---|---|---|---|
| Adult | 1 | −2 | 0 | −1 |
| Neonate (low noise) | 1 | −1 | −1 | −1 |
| Neonate (high noise) | 2 | −1 | −2 | −1 |

For example, Table 1 above illustrates a set of weighting functions for three clinical situations: an adult; a neonate in which noise (due, for example, to movement of the patient) is low, and a neonate in which noise is high. As described above, the weights W2, W3 and W4 are all negative to make up for corresponding likelihood factors for which lower values represent higher likelihoods. Though the weights in Table 1 are illustrated as integers, one skilled in the art will understand that the weights may be expressed in real numbers as well. One skilled in the art will also understand that different sets of weights may exist for more that just the clinical situations illustrated in Table 1. For example, further classifications may be made by sex, weight, age, health, etc. One skilled in the art will further understand that the weights could be varied dynamically. The weighting subsystem 127 produces one set of six weighted likelihood factors $WLF_i$s ($WLF_i(1)$, $WLF_i(2)$, $WLF_i(3)$ and $WLF_i(4)$) for each peak i identified by the IR spectral peak identification circuit 114 (of FIG. 1).

TABLE 2

| | WLF(1) | WLF(2) | WLF(3) | WLF(4) | FLF |
|---|---|---|---|---|---|
| P1-35 BPM | $WLF_1(1)$ | $WLF_1(2)$ | $WLF_1(3)$ | $WLF_1(4)$ | $\Sigma WLF(1)$ |
| P2-46 BPM | $WLF_2(1)$ | $WLF_2(2)$ | $WLF_2(3)$ | $WLF_2(4)$ | $\Sigma WLF(2)$ |
| P3-76 BPM | $WLF_3(1)$ | $WLF_3(2)$ | $WLF_3(3)$ | $WLF_3(4)$ | $\Sigma WLF(3)$ |
| P4-140 BPM | $WLF_4(1)$ | $WLF_4(2)$ | $WLF_4(3)$ | $WLF_4(4)$ | $\Sigma WLF(4)$ |
| P5-160 BPM | $WLF_5(1)$ | $WLF_5(2)$ | $WLF_5(3)$ | $WLF_5(4)$ | $\Sigma WLF(5)$ |

The arbitrator 128 receives all of the weighted likelihood factors WLFs from the weighting subsystem 127 and selects one of the IR FFT peak frequencies in response. Table 2 illustrates all of the WLFs generated for the IR FFT peaks illustrated in FIG. 2. In the illustrated embodiment, the $WLF_i$s for each peak i are summed, and the resulting sum is the final likelihood factor $FLF_i$ for that peak i. The peak having the highest FLF is selected at the peak representing the actual pulse rate by the arbitrator 128. One skilled in the art will understand that other methods of selecting one of the identified IR FFT peaks may be used.

The pulse rate and $SpO_2$ calculating and display circuit 130 calculates the pulse rate PLS from the frequency of the IR FFT peak selected by the arbitrator 128 as $$PLS = \frac{freq(IR\ FFT\ peak)}{60}.$$

The FFT magnitude values of the red and IR FFTs at the frequency location of the peak selected by the arbitrator 128, and at the dc frequency location, are then used to calculate the $SpO_2$ value in a known manner. These calculated values are then displayed on the display device.

Although the $SpO_2$ system has been described above generally in terms of hardware circuitry, one skilled in the art would understand that once multibit digital signals representing the red and IR light signals are generated by the signal processor 108, a processor, such as a microprocessor or digital signal processor, could be programmed to perform the functions illustrated in FIG. 1 and described in detail above. Such a processor could then control a display device to display the results of this processing.

What is claimed is:

1. Apparatus for estimating a physiological parameter from a physiological signal derived from patient blood, comprising:

a source of the physiological signal;

a characteristic identification processor, coupled to the physiological signal source, for identifying respective characteristics in the physiological signal;

at least one likelihood processor, coupled to the characteristic identification processor and deriving likelihood representative values from a function associating probability values with pulse rates, said values respectively corresponding to the identified characteristics and representing a probability that the corresponding identified characteristic is associated with said physiological parameter;

an arbitrator for selecting one of the identified characteristics in response to the likelihood representative values; and a computational processor, for estimating the physiological parameter responsive to the selected one of the identified characteristics.

2. The apparatus of claim 1 wherein the function associates probability values with pulse rates and said probability values are adjusted in response to at least one of, (a) a previously computed pulse rate and (b) a previously computed blood oxygen saturation representative value.

3. The apparatus of claim 1 wherein the characteristic identification processor comprises a peak identifying processor for identifying one or more peaks at respective corresponding frequencies in the spectrum of the physiological signal as characteristics of the physiological signal.

4. The apparatus of claim 3 wherein the peak identification processor comprises:

a fast Fourier transform (FFT) circuit, coupled to the physiological signal source, for generating a frequency spectrum, having respective magnitudes at associated frequencies, representing the physiological signal;

a peak locating processor, responsive to the spectrum, for identifying peaks in the respective magnitudes and the frequency associated with the peaks.

5. The apparatus of claim 4 further comprising a window filter coupled to the peak identification processor for generating a plurality of time domain signals window filtered at frequencies respectively corresponding to the identified peaks.

6. The apparatus of claim 5 wherein the window filter comprises:

a circuit selecting a subset of magnitudes in the frequency spectrum in the neighborhood of the frequency of each identified peak; and an inverse fast Fourier transform processor, for generating a time domain window filtered signal in response to the selected subset of magnitudes.

7. The apparatus of claim 3, wherein:

the frequency of each identified peak has an associated period; and one of the plurality of likelihood processors comprises:

a circuit for generating a plurality of time domain signals, each signal being the physiological signal window filtered in the neighborhood of the frequency of a respective corresponding identified peak;

a processor for generating a plurality of time delayed signals respectively corresponding to the plurality of time domain signals delayed by respective time intervals equal to one-half the period associated with the time domain signal; and a processor for generating a plurality of likelihood signals, each corresponding to a respective one of the identified peaks, representing degree of congruence of the time domain signal to the delayed time domain signal corresponding to the one of the identified peaks.

8. The apparatus of claim 7 wherein the time delayed signal generating processor delays the plurality of time domain signals by respective time intervals equal to (n+½) times the period associated with the time domain signal where n is an integer greater than or equal to zero.

9. The apparatus of claim 1 wherein:

the estimated physiological parameter comprises a patient pulse rate and the identified characteristics comprise peaks in the physiological signal and the physiological signal comprises a blood oxygen representative signal.

10. The apparatus of claim 1 further comprising a bandpass filter coupled between the physiological signal source and the characteristic identification processor.

11. A method for estimating pulse rate from a physiological signal derived from patient blood, comprising the steps of:

receiving a physiological signal;

identifying respective characteristics in said received physiological signal;

deriving likelihood representative values from a function associating probability values with pulse rates, said values respectively corresponding to the identified characteristics and representing a probability that the corresponding identified characteristic is associated with said physiological parameter;

selecting one of said identified characteristics in response to said likelihood representative values; and estimating said pulse rate using said selected one of said identified characteristics.

12. The method of claim 11, wherein the function associates probability values with pulse rates and said probability values are adjusted in response to at least one of, (a) a previously computed pulse rate and (b) a previously computed blood oxygen saturation representative value.

13. The method of claim 11, wherein the function is a probability density function.

14. The method of claim 11 wherein the identified characteristics comprise peaks in the physiological signal and the physiological signal comprises a blood oxygen representative signal.

15. The method of claim 11 wherein:

the physiological signal comprises first and second component signals; and including the steps of:

generating a first plurality of time domain signals, each signal being the first component signal window filtered in the neighborhood of the frequency of a respective corresponding identified peak;

generating a second plurality of time domain signals, each signal being the second component signal window filtered in the neighborhood of the frequency of a respective corresponding identified peak; and generating a plurality of likelihood signals, each corresponding to a respective one of the identified peaks, representing degree of congruence of the corresponding one of the first plurality of time domain signals, to the corresponding one of the second plurality of time domain signals.

16. The method of claim 11, wherein said step of deriving likelihood representative values comprises deriving a likelihood representative value corresponding to a particular identified characteristic from a function associating probability values with pulse rates, in response to an identified pulse rate corresponding to the particular identified characteristic.

17. The method of claim 11 further including the step of bandpass filtering data representing identified characteristics and deriving said likelihood representative values based on filtered identified characteristic representative data.

18. The method of claim 11 wherein:

the frequency of each identified peak has an associated period; and further including the step of:

generating respective pluralities of time delayed signals respectively corresponding to the first and second pluralities of time domain signals delayed by respective time intervals.

19. The method of claim 11 wherein said step of deriving likelihood representative values includes the step of generating a plurality of signals, respectively representing the probability that corresponding peak represents the physiological parameter.

20. The method of claim 19 including the steps of extracting the probability that the frequency location of each identified peak in the physiological signal represents the physiological parameter;

determining a degree of spread of the previously estimated physiological parameters; and generating a new probability density function.

21. The method of claim 20 including the step of scaling the probability density function.

22. The method of claim 11 wherein, said received physiological signal is derived from an $SpO_2$ sensor.

23. A method for estimating a physiological parameter from a physiological signal derived from patient blood, comprising the steps of:

receiving a physiological signal;

identifying respective characteristics in said received physiological signal;

deriving likelihood representative values from a function associating probability values with pulse rates, said values respectively corresponding to the identified characteristics and representing a probability that the corresponding identified characteristic is associated with said physiological parameter;

selecting one of said identified characteristics in response to said likelihood representative values; and estimating said physiological parameter using said selected one of said identified characteristics.

24. A method according to claim 23, including the step of bandpass filtering said received physiological signal and wherein said identifying step comprises identifying respective characteristics in said bandpass filtered received physiological signal.

* * * * *